United States Patent
Fior et al.

(10) Patent No.: US 10,137,025 B2
(45) Date of Patent: Nov. 27, 2018

(54) DEVICE AND METHOD FOR ELECTRIC STIMULATION OF MUSCLES INVOLVED IN HUMAN PHYSIOLOGICAL GAIT PATTERN AND BRACE TO SUPPORT AN ANATOMICAL JOINT WITH SUCH DEVICE

(71) Applicant: EVOMOTION GMBH, Lueneburg (DE)

(72) Inventors: Joerg Fior, Lueneburg (DE); Ralf Gentz, Lueneburg (DE)

(73) Assignee: EVOMOTION GMBH, Lueneburg (DE)

( * ) Notice: Subject to any disclaimer, the term of this patent is extended or adjusted under 35 U.S.C. 154(b) by 357 days.

(21) Appl. No.: 14/955,848

(22) Filed: Dec. 1, 2015

(65) Prior Publication Data
US 2016/0199208 A1    Jul. 14, 2016

(30) Foreign Application Priority Data
Dec. 2, 2014    (DE) .......................... 10 2014 117 663

(51) Int. Cl.
*A61F 5/01*    (2006.01)
*A61N 1/36*    (2006.01)
(Continued)

(52) U.S. Cl.
CPC ............ *A61F 5/0102* (2013.01); *A61B 5/112* (2013.01); *A61B 5/6828* (2013.01);
(Continued)

(58) Field of Classification Search
CPC ........ A61F 5/0102; A61F 5/01; A61F 5/0195; A61F 5/0127; A61F 5/0585;
(Continued)

(56) References Cited

U.S. PATENT DOCUMENTS

| | | | |
|---|---|---|---|
| 6,836,744 B1 * | 12/2004 | Asphahani | A43D 1/02 377/24.2 |
| 2004/0082979 A1 | 4/2004 | Tong et al. | |

(Continued)

OTHER PUBLICATIONS

German Office Action from German Application No. 10 2014 117 663.4 dated Dec. 2, 2014 with an English Translation.

*Primary Examiner* — Ophelia A Hawthorne
(74) *Attorney, Agent, or Firm* — FisherBroyles, LLP; Robert Kinberg (57) ABSTRACT

A device for electrical stimulation of muscles involved in the physiological gait of a human includes an element for electrical muscle stimulation. A sensor detects information relevant to the muscle stimulation. The sensor includes a gyroscope constructed to detect information including an angular speed ω and a swing direction in an extension direction and flexion direction of an anatomical lower leg of the human. An evaluation unit, including a microprocessor, evaluates the information detected by the gyroscope, determines a defined switching time for the muscle stimulation on the basis of the angular speed ω and the swing direction, and transmits the determined switching time to a control and regulation unit that triggers muscle stimulation by the element in response to receipt of the determined switching time.

11 Claims, 4 Drawing Sheets

(51) Int. Cl.
  *A61B 5/00*     (2006.01)
  *A61N 1/18*     (2006.01)
  *G01C 22/00*    (2006.01)
  *A61B 5/11*     (2006.01)

(52) U.S. Cl.
  CPC .............. *A61B 5/7282* (2013.01); *A61F 5/01* (2013.01); *A61N 1/18* (2013.01); *A61N 1/36003* (2013.01); *A61N 1/36014* (2013.01); *G01C 22/00* (2013.01); *A61B 5/1116* (2013.01); *A61B 5/1121* (2013.01); *A61B 5/4851* (2013.01); *A61B 5/6811* (2013.01); *A61B 2505/09* (2013.01); *A61B 2562/0219* (2013.01)

(58) Field of Classification Search
  CPC ...... A61F 5/0111; A61B 5/112; A61B 5/6828; A61B 5/7282; A61B 5/1116; A61B 5/1121; A61B 5/4851; A61B 5/6811; A61B 2505/09; A61B 2562/0219; A61N 1/18; A61N 1/36003; A61N 1/36014; G01C 22/00
  See application file for complete search history.

(56) References Cited

U.S. PATENT DOCUMENTS

| | | |
|---|---|---|
| 2004/0172097 A1 | 9/2004 | Brodard et al. |
| 2011/0137375 A1* | 6/2011 | McBride ............ A61N 1/36003 607/49 |
| 2014/0128939 A1 | 5/2014 | Embrey et al. |

* cited by examiner

DEVICE AND METHOD FOR ELECTRIC STIMULATION OF MUSCLES INVOLVED IN HUMAN PHYSIOLOGICAL GAIT PATTERN AND BRACE TO SUPPORT AN ANATOMICAL JOINT WITH SUCH DEVICE

CROSS-REFERENCE TO RELATED APPLICATIONS

This application claims priority to German Application No. 10 2014 117 663.4 filed Dec. 2, 2014, the disclosure of which is incorporated herein by reference in its entirety.

BACKGROUND OF INVENTION

The invention concerns a device designed and adapted for electrical muscle stimulation of muscles involved in the physiological gait of a human, comprising an element for electrical muscle stimulation, a sensor for detecting information relevant to the muscle stimulation, and a control and/or regulation unit for triggering the muscle stimulation on the basis of the information detected by the sensor.

The invention furthermore concerns an orthosis, or brace, designed and adapted for supporting at least the anatomical lower leg of a human, comprising a lower leg support element and a foot support element connected to the lower leg support element.

The invention also concerns a method for electrical muscle stimulation of muscles involved in the physiological gait of a human, by means of a device for muscle stimulation, comprising. the steps: determining a switching time for the muscle stimulation by means of a sensor, transmitting the switching time to a control and/or regulation unit, triggering the muscle stimulation by the control and/or regulation unit on the basis of the information detected by the sensor, and stimulating muscles by means of an element for electrical muscle stimulation.

Such devices and methods are used in particular in orthopedics in order to achieve a stimulation of the muscles involved in the physiological gait of a human in patients with a muscle and/or joint and/or bone weakness, for example because of a stroke or a paraplegia or other disorder adversely affecting the gait of a human. The orthosis joints are used in particular in patients with a chronic disease, for patients during therapy and as a walking or standing aid for patients with weakened or contracted musculature.

A plurality of muscles or muscle groups are involved in the physiological gait of the human. Purely as an example, these include the calf muscles, the trunk muscles, the buttock muscles and also the arm muscles. In known illness patterns, for example following a stroke, control of the muscle by the brain via the respective nerve pathways is disrupted. This means that the muscles can fully or partly no longer be controlled. This effect necessarily leads to a muscular atrophy of the muscles which are no longer controlled and therefore no longer involved in the physiological gait. For example with a stroke, as a result a so-called flaccid paralysis can occur. Spasticity can also occur. Both flaccid paralysis and spasticity, due to lack of control and corresponding lack of activity, lead to atrophy of the muscles concerned. Thus walking, for example supported by an orthosis, becomes ever more difficult and unsafe for the people concerned. In other words, the natural gait or individual walking phases of a walk cycle may no longer be supported, or only within limitations. In particular, muscular atrophy leads to a deteriorating condition and consequently an unsafe gait. Due to the loss of control of the muscles or muscle fibers, individual phases of the gait, e.g. the push-off phase during walking, are not supported, whereby a defective gait results.

In principle, it is known to stimulate electrically the weakened muscles and/or muscles no longer controlled. For this purpose bandages or stockings are known. These bandages/stockings known from the trade, as elements for electrical muscle stimulation, normally serve to stimulate the foot-lifting muscles to lift the feet during the swing phase. The relevant information detected by the sensor is in particular the time of muscle stimulation. 'To trigger the electrical muscle stimulation, a signal from a pressure sensor as a sensor is used, which transmits the signal via a cable to a control and/or regulation unit. The pressure sensor is arranged below the foot and normally fitted in the patient's shoe. The muscle stimulation is triggered at a pressure level to be determined. The problem with the known solution lies in determining the correct pressure. Because the pressure sensor is carried in a shoe, the problem exists that the shoe is laced up sometimes more tightly and sometimes less tightly, which has a direct effect on the pressure and hinders the determination of a precisely defined time of muscle stimulation. On the one hand, pressure is applied permanently to the pressure sensor. On the other hand, pressure is determined by the pressure sensor below the foot over almost the entire standing phase which accounts for around 60% of the walking cycle, whereby determination of an optimal time of muscle stimulation is imprecise. A further disadvantage is that because of the problem of space below the foot, the signal from the pressure sensor is transmitted by means of a wire to the control and/or regulation unit. This configuration makes handling more difficult and is susceptible to damage. Also, a temporally incorrect and/or overly intensive (over-long) muscle stimulation is perceived by the patient as disruptive or uncomfortable.

SUMMARY OF THE INVENTION

The invention is therefore based on the object of proposing a device which is simple to handle and which guarantees a targeted and precise muscle stimulation. The object is furthermore to propose a corresponding method and corresponding orthosis.

This object is achieved by a device of the above type, wherein in addition the sensor comprises a single gyroscope which is designed and adapted to detect the angular speed ω, on the one hand, and the swing direction in the extension direction and flexion direction, on the other hand, of the anatomical lower leg of the human, and in that the device has an evaluation unit with a microprocessor for evaluating the information supplied by the gyroscope and for determining a defined switching time for the muscle stimulation on the basis of the angular speed ω and the swing direction, and for transmitting the switching time determined to the control and/or regulation unit. By determination or knowledge of the angular speed ω and the swing direction of the lower leg, the precise time of a fixedly defined point in the walking phase of a human can be determined. From this information, the program or software stored on the microprocessor can calculate the precise switching time for the muscle stimulation. With the embodiment of the device according to the invention, all muscles required for the physiological gait e.g. the calf muscles, buttock muscles, trunk muscles and also arm muscles, can be electrically stimulated optimally and precisely at the correct time. Because of the configuration according to the invention, the device can be used wirelessly, which facilitates handling in particular for the patient.

The microprocessor of the evaluation unit may be programmed to determine a fixedly defined reference switching time in the physiological walking phase of the human, and starting from the reference switching time, to determine further switching times in different walking phases of a walking cycle. In this way, a muscle stimulation can be determined in a targeted fashion for each walking phase of the patient. Starting from the knowledge that a step cycle, i.e. the phase from a first heel contact of e.g. the right foot to the next subsequent heel contact of the same foot, is divided into approximately 60% standing phase (phase in which the foot is in contact with the ground) and approximately 40% swing phase (phase in which the toe is lifted from the ground, until the foot is placed with the heel back on the ground), the microprocessor can determine each individual walking phase precisely from the reference switching time, in order to trigger any necessary muscle stimulation. "Approximate" values are cited deliberately since these values may differ slightly from person to person, so that "approximate" values are used as average values.

In an embodiment of the invention, the microprocessor of the evaluation unit is programmed to determine a fixedly defined reference switching time for triggering the muscle stimulation, based on the information of the positive swing direction of the lower leg, on the one hand, namely in the extension direction, and an angular speed of $\omega=0$, on the other hand. So starting from the time determined at which the heel is directly before contact with the ground, the so-called "Initial Stance Phase", all times of the individual walking phases in a typical walking cycle for the next step can be determined which may be used as a switching time for the electrical muscle stimulation.

In a further embodiment the sensor may also comprises an acceleration sensor which is designed and adapted for calibrating the gyroscope. With the acceleration sensor, the orientation—namely in particular the swing direction of the lower leg—can be specified precisely. The acceleration sensor allows determination of the location and position of the gyroscope and hence its orientation.

A further object of the invention is the provision of an orthosis, or brace, which comprises a device for electrical muscle stimulation.

The advantages resulting from the orthosis according to the invention have already been presented in connection with the device designed and adapted for stimulation of muscles involved in the physiological gait of a human, so to avoid repetition, reference is made to the corresponding passages.

Advantageously, the sensor comprising the gyroscope is assigned to the lower leg support element, and the element for electrical muscle stimulation is designed and adapted as a sleeve, bandage or similar for application to the calf muscles of the lower leg. With this design, in particular the muscles involved in the push-off phase of the foot are stimulated, whereby the patient wearing the device is accelerated into the forward motion.

In one embodiment, the lower leg support element is designed as a lower leg half shell, and the foot support element is designed as a foot shell, wherein the foot support element and the lower leg support element are connected together in articulated fashion via an orthosis joint. With this design, an improved support function can be provided for the lower leg compared with conventional stockings or bandages, so that the muscle stimulation can be targeted more directly at the calf muscles and their switching time, and together with the improved support function, the patient's gait can be optimized.

In another embodiment, the orthosis may comprise an upper leg support element which is connected in articulated fashion by means of an orthosis joint to the lower leg support element, wherein the orthosis joint has a joint upper part and a joint lower part which is connected in articulated fashion to the joint upper part, and a blocking element for automatic unlocking and locking of the orthosis joint in any arbitrary position, wherein the orthosis joint is controllable relative to the locking and unlocking by the sensor of the device for electrical muscle stimulation. Due to the leg orthosis as a whole, the gait of a patient can be stabilized particularly well and approximated to the physiological gait, since a combination of optimized support and optimized muscle stimulation is guaranteed. On the one hand, the gyroscope and the evaluation unit can ensure, for each walking speed and each angular position of the orthosis, that the orthosis joint can be securely locked on extension before the heel makes contact with the ground. On the other hand, the gyroscope and the evaluation unit can determine the optimal switching time for the muscle stimulation, so that in parallel with a high walking safety, a high support of the physiological gait is ensured in all walking phases.

In a further aspect of the invention, there is provided a method wherein the angular speed $\omega$ and the swing direction in the extension direction and flexion direction of the anatomical lower leg of the human are detected by means of a gyroscope, and on the basis of the information supplied by the gyroscope, by means of an evaluation unit comprising a microprocessor, a defined switching time for the electrical muscle stimulation is determined and transmitted to the control and/or regulation unit.

A microprocessor may be used to determine a fixedly defined reference switching time in the physiological walking phase of the human, and on the basis of this reference switching time, further switching times in different walking phases of a walking cycle may be determined.

In a further embodiment, the fixedly defined reference switching time is determined on the basis of information about the positive swing direction of the lower leg, on the one hand, namely in the extension direction, and the angular speed $\omega=0$, on the other hand.

According to an embodiment of the invention, the calf muscles and/or further muscles involved in the physiological gait, such as e.g. the trunk muscles, the buttock muscles, the arm muscles, may be electrically stimulated via the reference switching point and/or the further switching points.

The advantages resulting from the method according to the invention have already been presented in relation to the device and the orthosis, so to avoid repetition, reference is made to the corresponding passages.

BRIEF DESCRIPTION OF THE DRAWINGS

Additional features and refinements of the invention arise from the following detailed description of the invention, when considered in connection with the accompanying drawings, wherein.

DETAILED DESCRIPTION OF THE INVENTION

The device shown in the drawing serves for stimulating the calf muscles of an anatomical human leg. Evidently, the device may also be used for stimulating other muscles involved in the physiological gait, and for stimulating animal musculature. The shown devices may be used as an independent orthopedic aid and/or in conjunction with orthoses and/or prostheses.

The device 10 shown in the drawing is designed and adapted for electrical muscle stimulation of muscles involved in the physiological gait of a human, and comprises an element 11 for electrical muscle stimulation, a sensor 12 for detecting information relevant for the muscle stimulation, and a control and/or regulation unit 13 for triggering the muscle stimulation of the basis of the information detected by the sensor 12.

This device 10 according to the invention is characterized in that the sensor 12 comprises a single gyroscope 14 which is designed and adapted to detect the angular speed $\omega$, on the one hand, and the swing direction in the extension direction and flexion direction, on the other hand, of the anatomical lower leg 15 of the human, and in that the device 10 comprises an evaluation unit 16 with a microprocessor for evaluating the information supplied by the gyroscope 14 and for determining a defined switching time for the muscle stimulation on the basis of the angular speed $\omega$ and the swing direction, and for transmitting the switching time determined to the control and/or regulation unit 13.

Such gyroscopes 14 or also gyroscopic sensors are precise and reliable when measuring angular speeds and determining the swing direction of the lower leg 15 if they are assigned to the lower leg 15 without relative movement. In other words, the gyroscope 14 attached in any manner, i.e. directly or indirectly, to the lower leg 15 supplies the information about the angular speed $\omega$ with which the leg, or more precisely the lower leg 15, moves forward in the extension direction or backward in the flexion direction. With this information, according to the invention at least one and preferably however a plurality of switching points can be determined for the electrical muscle stimulation of different muscles and muscle groups.

Figure 1:
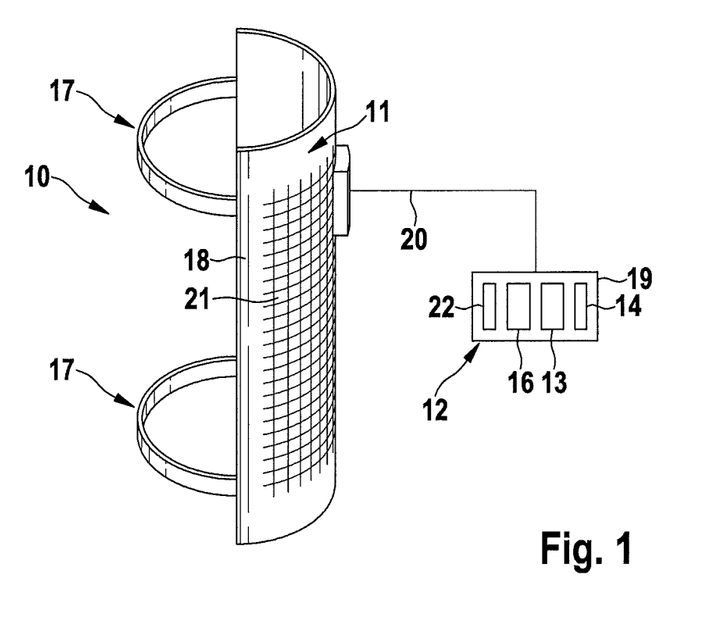
FIG. 1 is a diagrammatic depiction and partial block circuit diagram of a device for muscle stimulation in which the sensor, on the one hand, and the element for muscle stimulation, on the other hand, are designed as separate components and are connected together only via a signal line.

FIG. 1 shows a device 10 in which the element 11 for muscle stimulation is a sleeve 18 equipped with closing elements 17. The element 11 may however also be a stocking, a bandage or other aid suitable for muscle stimulation which can lie closely against the respective musculature. In the embodiment shown, the element 11 is designed and adapted for fitting to the calf muscles of a human lower leg 15. In other embodiments not shown explicitly, the element 11 may also be used for attachment to the buttock musculature e.g. in the form of trousers, to the trunk musculature e.g. in the form of a shirt, or to the arm musculature e.g. in the form of a sleeve. The sensor 12 is preferably arranged in a common housing 19. In the preferred embodiment according to FIG. 1, the control and/or regulation unit 13, the gyroscope 14 and the evaluation unit 16 are arranged in the housing 19 and connected to the element 11 by means of a connection 20 which may be hard-wired or wireless. By the separation of the components i.e. the housing 19 with the components arranged therein, on the one hand, and the element 11, on the other hand, the housing 19 with the sensor 12 can always be positioned on the lower leg 15 independently of the configuration and attachment of the element 11, in order to detect and determine the information necessary for control and/or regulation of the element 11. In the embodiment according to FIG. 2, the sensor 12, i.e. the control and/or regulation unit 13, the gyroscope 14 and the evaluation unit 16, are integral parts of the element 11. In both embodiments, the control and/or regulation unit 13 is connected to the means 21 triggering the electrical stimulation.

Figure 2:
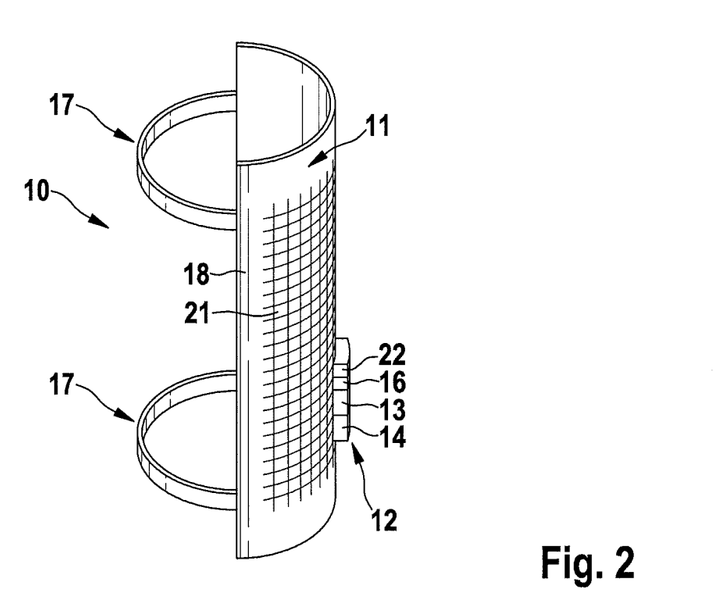
FIG. 2 is a diagrammatic depiction of a device for muscle stimulation in which the sensor is directly assigned to the element for muscle stimulation.

The microprocessor of the evaluation unit 16 may be programmed to determine a fixedly defined reference switching time in the physiological walking phase of the human, and starting from the reference switching time, to determine further switching times in different walking phases of a walking cycle. For this, the microprocessor has a software by means of which, from the information from the sensor 12, arbitrary switching points can be calculated for each muscle involved in the gait. From one or more special times of the walking cycle, by means of the software a prognosis can be calculated for all further typical times of the walking phase of the walking cycle, and at least one element 11 for muscle stimulation, preferably however a plurality of such elements 11 for muscle stimulation, can be controlled which then stimulate the different muscles at the calculated switching time.

The microprocessor of the evaluation unit 16 may be programmed to determine the fixedly defined reference switching time for triggering the muscle stimulation based on the information on the positive swing direction of the lower leg, on the one hand, namely in the extension direction, and the angular speed $\omega=0$, on the other hand. The reference switching time can also be calculated on the basis of other information determined by the sensor.

In the shown embodiments, the sensor 12 comprises additionally and optionally an acceleration sensor 22 which is designed and adapted for calibrating the gyroscope 14. The gyroscope 14 in any case is arranged below the anatomical knee joint when properly used. Preferably, the acceleration sensor 22 is also arranged below the anatomical knee joint.

Figure 3:
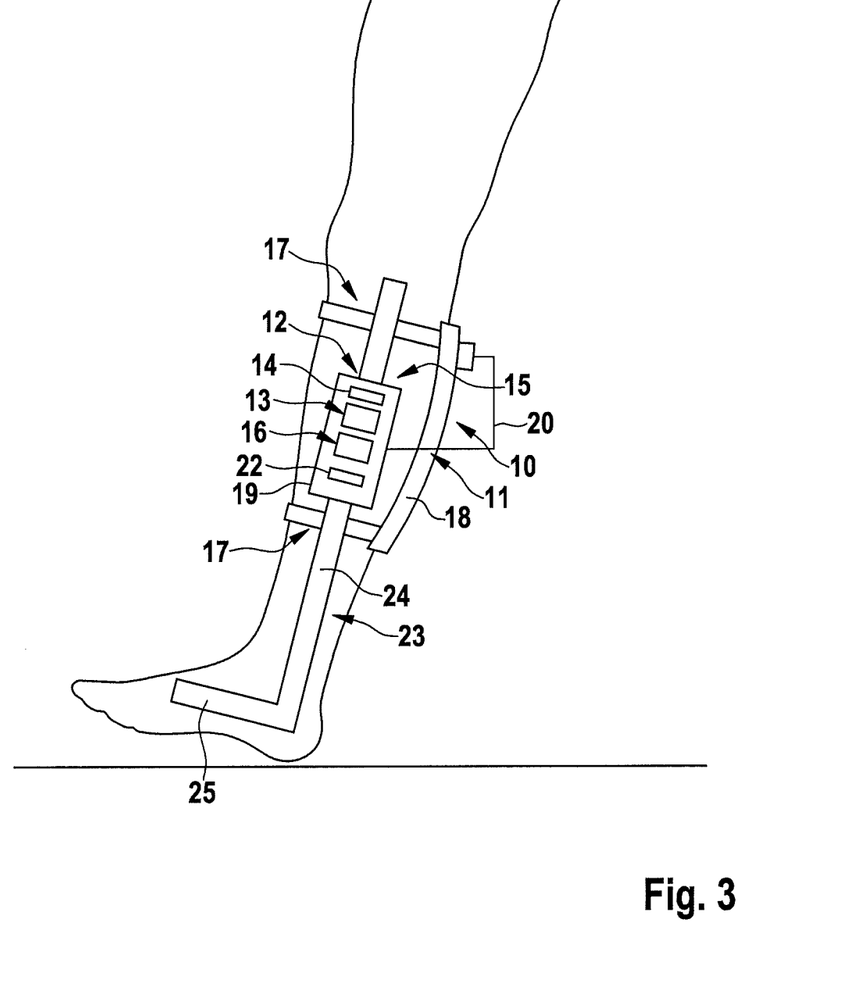
FIG. 3 is a diagrammatic depiction of an anatomical leg in the extension position, to which a first embodiment of an orthosis for the lower leg is assigned with the device according to FIGS. 1 and 2.

FIG. 3 shows a device 10 for electrical muscle stimulation in conjunction with an orthosis 23. The orthosis 23 is designed and adapted to support at least the anatomical lower leg 15 of a human, and comprises a lower leg support element 24 and a foot support element 25 which is connected fixedly or in articulated fashion to the lower leg support element 24. This orthosis 23 according to the invention is distinguished in that the device 10 is designed and adapted in the manner described above. In the depiction shown, the support elements are shown as simple rails. The support elements may also however be configured as half shells or as a grid structure or similar.

Figure 4:
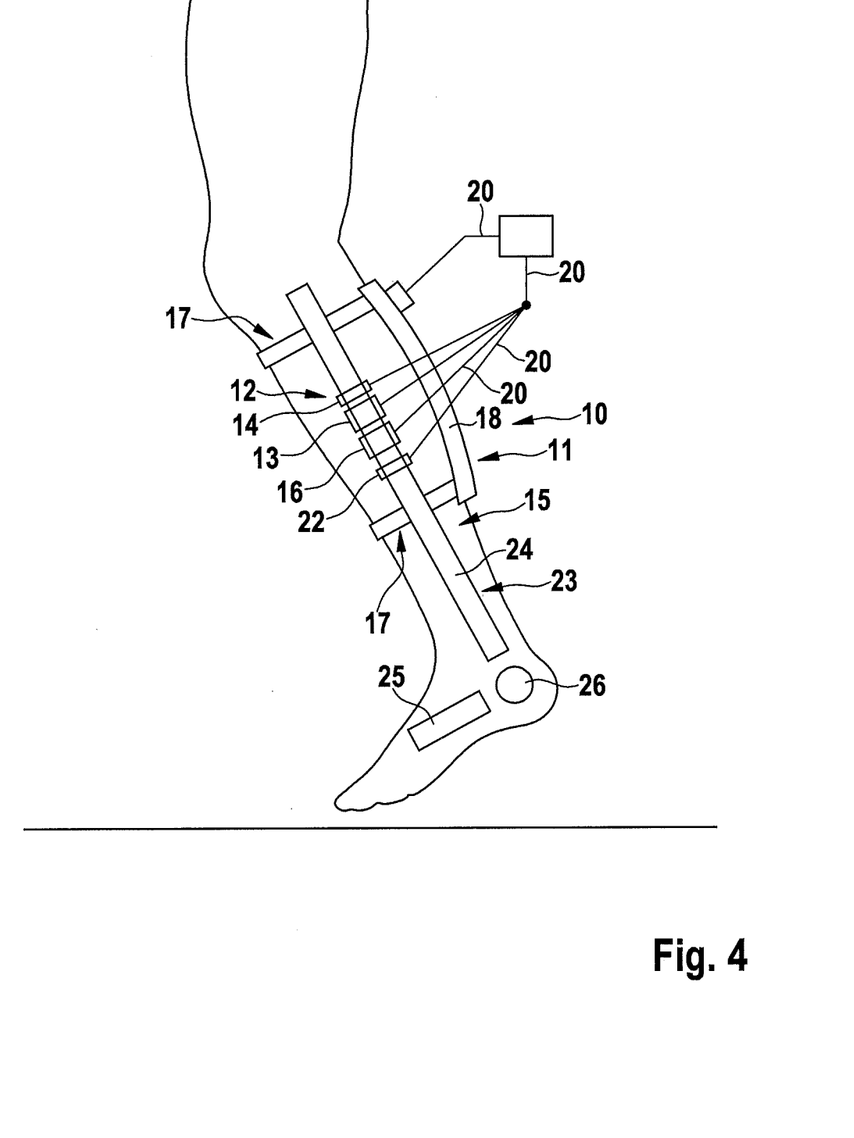
FIG. 4 is a diagrammatic depiction of an anatomical leg in the flexion position, to which a further embodiment of an orthosis for the lower leg is assigned with the device according to FIGS. 1 and 2.

The sensor 12 comprising the gyroscope 14 is assigned to the lower leg support element 24. The element 11 for electrical muscle stimulation is designed and adapted as a sleeve 18 for attaching to the calf muscles of the lower leg 15. In FIG. 3, the connection between the lower leg support element 24 and the foot support element 25 is rigid. In FIG. 4, an orthosis joint 26 is arranged between the lower leg support element 24 and the foot support element 25 for articulated connection.

Figure 5:
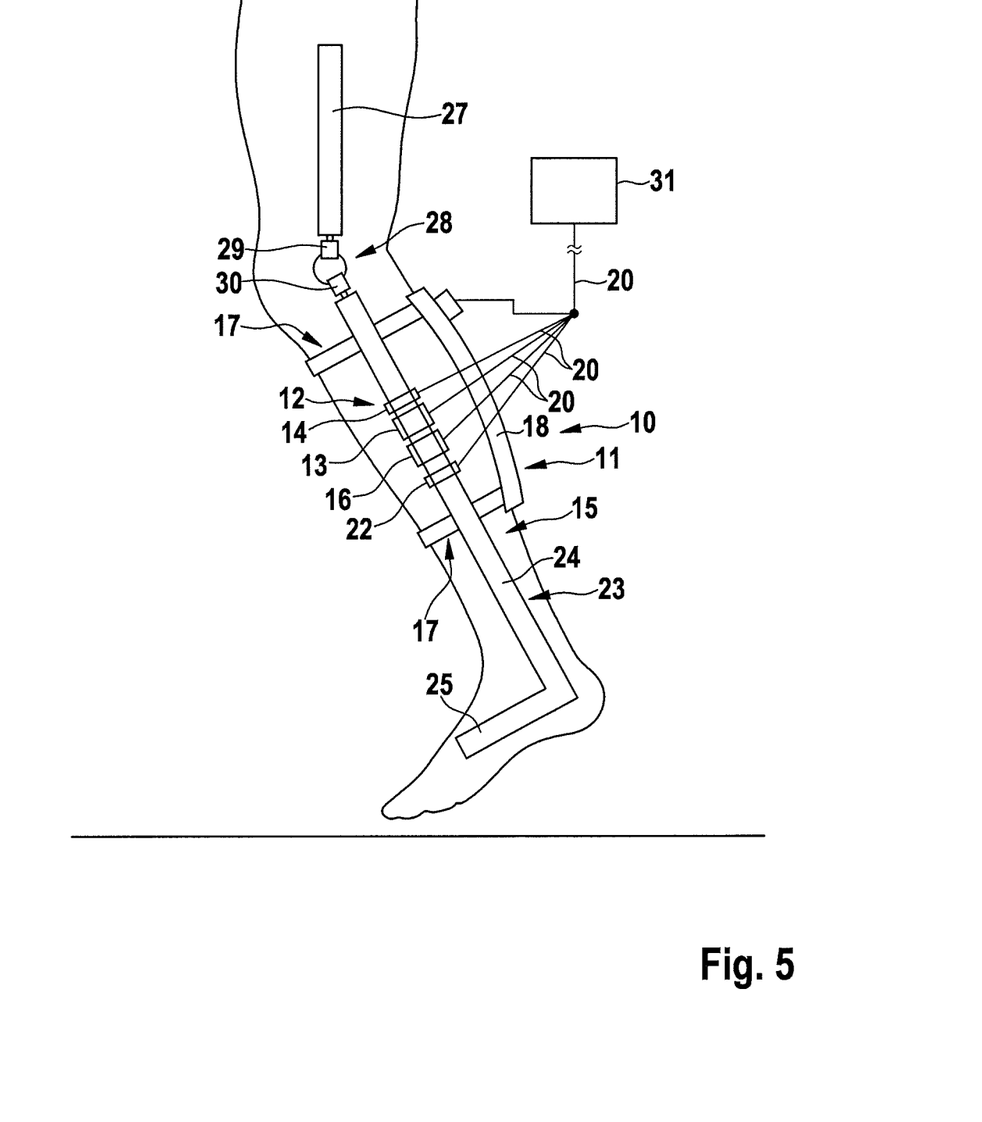
FIG. 5 is a diagrammatic depiction of an orthosis for the entire leg in the flexion position with an orthosis joint in the knee area and the device for electric muscle stimulation in the lower leg area, wherein the sensor of the device for electrical muscle stimulation is designed and adapted additionally for locking and unlocking the orthosis joint in the knee area independently of the incline of the lower leg.

FIG. 5 shows an orthosis 23 which additionally comprises an upper leg support element 27 which is connected in articulated fashion to the lower leg support element 24 by means of an orthosis joint 28. The orthosis joint 28 comprises a joint upper part 29 and a joint lower part 30 connected in articulated fashion to the joint upper part 29, and a blocking element (not shown) for automatic unlocking and locking of the orthosis joint 28 in any arbitrary position. The orthosis joint 28 may be controlled for locking and unlocking by means of the sensor 12 of the device 10 for electrical muscle stimulation. In other words, the information detected by the gyroscope 14 and evaluated by the evaluation unit 16 may also be used to determine the optimum locking and unlocking time for the orthosis joint 28, independently of the incline of the lower leg 15, and also to determine a defined switching time for the muscle stimulation, which constitutes a compact and easily usable support for the patient.

In the embodiment according to FIG. 5, in addition a control unit 31 is provided. By means of the control unit 31, direct and immediate access or intervention in the control/regulation system is possible for the patient and/or an orthotics specialist.

The method according to the invention is explained in more detail below with reference to drawings.

The method serves for electrical muscle stimulation of muscles involved in the physiological gait of a human by means of a device 10 for muscle stimulation. First a switching time for the muscle stimulation is determined by means of a sensor 12. The determined switching time is transmitted to a control and/or regulation unit 30. On the basis of the information detected by the sensor 12, the control and/or regulation unit 13 triggers the muscle stimulation, whereupon the muscles are stimulated by means of an element 11 for electrical muscle stimulation.

This method according to the invention is distinguished in that the angular speed $\omega$ and the swing direction in the extension direction and flexion direction of the anatomical lower leg 15 of the human are detected by means of a gyroscope 14, and on the basis of the information supplied by the gyroscope 14, by means of an evaluation unit 16 comprising a microprocessor, a defined switching time for the electrical muscle stimulation is determined and transmitted to the control and/or regulation unit 13.

The method may be executed with the device 10 described above. By means of the microprocessor, a fixedly defined reference switching time in the physiological walking phase of the human is determined. Starting from this reference switching time, further switching times are determined in different walking phases of a walking cycle. The fixedly defined reference switching time may be determined on the basis of the information on the positive swing direction of the lower leg 15, on the one hand, namely in the extension direction, and the angular speed of $\omega=0$, on the other hand. Via the reference switching time and/or the further switching times, in particular the calf muscles and/or further muscles involved in the physiological gait are electrically stimulated, such as e.g. the trunk muscles, buttock muscles, and arm muscles.

If a walking cycle (heel with ground contact, swing phase, same heel with ground contact) is set e.g. at 100%, and the reference switching time at $\omega=0$ in the extension direction is set at 0%, with knowledge of the division of a walking cycle into 60% standing phase and 40% swing phase, the further switching time for stimulation of the calf muscles can be determined. For another walking phase, e.g. during the swing phase of the lower leg 15, it may be helpful to stimulate the trunk muscles in order to better maintain equilibrium or balance. Accordingly, starting from the reference switching time after 70% of the walking cycle, the trunk muscles can be controlled with a corresponding element 11 for muscle stimulation.

The invention has been described in detail with respect to various embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

What is claimed is:

1. A method for electrical stimulation of muscles involved in the physiological gait of a human by a device for muscle stimulation, comprising: detecting, by a sensor comprising a gyroscope, information including an angular speed $\omega$ and a swing direction in an extension direction and flexion direction of an anatomical lower leg of the human; determining, by an evaluation unit comprising a microprocessor, a defined switching time for the electrical muscle stimulation on the basis of the information from the sensor; transmitting the switching time to a control and regulation unit; and triggering an element for electrical muscle stimulation by the control and regulation unit in response to receipt of the switching time.

2. The method as claimed in claim 1, wherein the determining includes determining a fixedly defined reference switching time in the physiological walking phase of the human, and, on the basis of the reference switching time, determining further switching times in different walking phases of a walking cycle.

3. The method as claimed in claim 1, wherein the determining includes determining a fixedly defined reference switching time on the basis of information on the positive swing direction of the lower leg in the extension direction and on the angular speed $\omega=0$.

4. The method as claimed claim 2, further including electrically stimulating at least one of the calf muscles and further muscles involved in the physiological gait upon reaching at least one of the reference switching point and the further switching times.

5. A device for electrical stimulation of muscles involved in the physiological gait of a human, comprising: an element for electrical muscle stimulation; a sensor to detect information relevant to the muscle stimulation, wherein the sensor comprises a single gyroscope constructed to detect information including an angular speed $\omega$ and a swing direction in an extension direction and flexion direction of an anatomical lower leg of the human; an evaluation unit including a microprocessor to evaluate the information detected by the gyroscope and to determine a defined switching time for the muscle stimulation on the basis of the angular speed $\omega$ and the swing direction, and to transmit the determined switching time; and a control and regulation unit to trigger muscle stimulation by said element in response to receipt of the determined switching time.

6. The device as claimed in claim 5, wherein the microprocessor of the evaluation unit is programmed to determine a fixedly defined reference switching time in a physiological walking phase of the human, and starting from a reference switching time, to determine further switching times in different walking phases of a walking cycle.

7. The device as claimed in claim 5, wherein the microprocessor of the evaluation unit is programmed to determine a fixedly defined reference switching time for triggering the muscle stimulation based on information of a positive swing direction of the lower leg, on the one hand, in the extension direction, and an angular speed of $\omega=0$, on the other hand.

8. The device as claimed in claim 5, wherein the sensor further comprises an acceleration sensor constructed to calibrate the gyroscope.

9. An orthosis designed and adapted for supporting at least an anatomical lower leg of a human, comprising a lower leg support element and a foot support element connected to the lower leg support element, wherein the orthosis further comprises a device for electrical muscle stimulation as claimed in claim 5.

10. The orthosis as claimed in claim 9, wherein the sensor comprising the gyroscope is assigned to the lower leg support element, and the element for electrical muscle stimulation comprises a sleeve, bandage or similar for application to the calf muscles of the lower leg.

11. The orthosis as claimed in claim 9, wherein the lower leg support element comprises a lower leg half shell, and the foot support element comprises a foot shell, wherein the foot support element and the lower leg support element have an articulated connection to one another via an orthosis joint.

* * * * *